United States Patent
Sharma et al.

(10) Patent No.: US 8,913,248 B2
(45) Date of Patent: Dec. 16, 2014

(54) SYSTEMS AND METHODS FOR IMPROVED BALANCED DETECTION IN OPTICAL COHERENCE TOMOGRAPHY IMAGING

(75) Inventors: Utkarsh Sharma, San Ramon, CA (US); Lingfeng Yu, Irvine, CA (US); Alexandre R. Tumlinson, San Leandro, CA (US); Matthew J. Everett, Livermore, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 163 days.

(21) Appl. No.: 13/489,368

(22) Filed: Jun. 5, 2012

(65) Prior Publication Data

US 2013/0010302 A1    Jan. 10, 2013

Related U.S. Application Data (60) Provisional application No. 61/493,858, filed on Jun. 6, 2011.

(51) Int. Cl.
| | |
|---|---|
| G01B 9/02 | (2006.01) |
| G01B 11/02 | (2006.01) |
| A61B 5/00 | (2006.01) |
| A61B 3/10 | (2006.01) |

(52) U.S. Cl.
CPC .......... *A61B 5/0066* (2013.01); *G01B 9/02004* (2013.01); *G01B 9/0207* (2013.01); *G01B 9/02091* (2013.01); *G01B 9/02058* (2013.01); *A61B 3/102* (2013.01)
USPC .......................................... 356/479; 356/497

(58) Field of Classification Search
CPC ........... G01B 9/02004; G01B 9/02091; G01B 9/02041; A61B 3/102; A61B 5/0066
USPC .................. 356/497, 479; 351/206, 210, 221
See application file for complete search history.

(56) References Cited

U.S. PATENT DOCUMENTS

| | | | |
|---|---|---|---|
| 4,976,512 A | * | 12/1990 | Safaai-Jazi ............... 385/30 |
| 5,134,276 A | | 7/1992 | Hobbs |
| 6,657,727 B1 | | 12/2003 | Izatt et al. |
| 6,927,860 B2 | | 8/2005 | Podoleanu et al. |
| 7,388,672 B2 | | 6/2008 | Zhou et al. |

(Continued)

FOREIGN PATENT DOCUMENTS

| | | |
|---|---|---|
| WO | 02/37075 A2 | 5/2002 |
| WO | 2005/047813 A1 | 5/2005 |

OTHER PUBLICATIONS

International Search Report and Written Opinion received for PCT Patent Application No. PCT/EP2012/060956, mailed on Sep. 10, 2012, 10 pages.

(Continued)

*Primary Examiner* — Kara E Geisel
*Assistant Examiner* — Dominic J Bologna
(74) *Attorney, Agent, or Firm* — Morrison & Foerster LLP (57) ABSTRACT

Systems and methods for reducing noise in balanced detection based optical coherence tomography (OCT) systems are described. Embodiments including both optical hardware and electronic based solutions to spectrally filter and attenuate the source reference light in optical coherence tomography in an effort to reduce RIN and FPN noise in OCT systems are presented. A novel application to electronic balanced detection schemes in which a single source of reference detection is balanced against the interferometric signals from multiple interferometers is also presented.

31 Claims, 8 Drawing Sheets

(56) References Cited

U.S. PATENT DOCUMENTS

| | | | |
|---|---|---|---|
| 2002/0167718 A1* | 11/2002 | Falquier et al. | 359/341.1 |
| 2004/0218189 A1* | 11/2004 | Izatt et al. | 356/479 |
| 2004/0233457 A1 | 11/2004 | Podoleanu et al. | |
| 2005/0018201 A1* | 1/2005 | de Boer et al. | 356/479 |
| 2008/0117431 A1* | 5/2008 | Teramura | 356/511 |
| 2008/0140328 A1* | 6/2008 | Kuroiwa | 702/66 |
| 2009/0086213 A1* | 4/2009 | Masuda | 356/479 |
| 2011/0102802 A1* | 5/2011 | Izatt et al. | 356/479 |
| 2011/0228280 A1 | 9/2011 | Schmitt et al. | |
| 2012/0026463 A1* | 2/2012 | Makihira et al. | 351/206 |

OTHER PUBLICATIONS

Chen et al., "Spectrally Balanced Detection for Optical Frequency Domain Imaging", Optics Express, vol. 15, No. 25, Dec. 10, 2007, pp. 16390-16399.

Choma et al., "Sensitivity Advantage of Swept Source and Fourier Domain Optical Coherence Tomography", Optics Express, vol. 11, No. 18, Sep. 8, 2003, pp. 2183-2189.

Drexler et al., "In Vivo Ultrahigh-Resolution Optical Coherence Tomography", Optics Letters, vol. 24, No. 17, Sep. 1, 1999, pp. 1221-1223.

Houser et al., "Balanced Detection Technique to Measure Small Changes in Transmission", Applied Optics, vol. 33, No. 6, Feb. 20, 1994, pp. 1059-1062.

Leitgeb et al., "Ultrahigh Resolution Fourier Domain Optical Coherence Tomography", Optics Express, vol. 12, No. 10, May 17, 2004, pp. 2156-2165.

Leitgeb et al., "Performance of Fourier Domain Vs. Time Domain Optical Coherence Tomography", Optics Express vol. 11, No. 8, Apr. 21, 2003, pp. 889-894.

Moon et al., "Normalization Detection Scheme for High-Speed Optical Frequency-Domain Imaging and Reflectometry", Optics Express, vol. 15, No. 23, Nov. 12, 2007, pp. 15129-15146.

Rollins et al., "Optimal Interferometer Designs for Optical Coherence Tomography", Optics Letters, vol. 24, No. 21, Nov. 1, 1999, pp. 1484-1486.

Yun et al., "High-Speed Optical Frequency Domain Imaging", Optics Express, vol. 11, No. 22, Nov. 3, 2003, pp. 2953-2963.

Yun et al., "High-Speed Spectral-Domain Optical Coherence Tomography at 1.3 μm Wavelength", Optics Express, vol. 11, No. 26, Dec. 29, 2003, pp. 3598-3604.

\* cited by examiner

SYSTEMS AND METHODS FOR IMPROVED BALANCED DETECTION IN OPTICAL COHERENCE TOMOGRAPHY IMAGING

PRIORITY

This application claims priority to provisional application Ser. No. 61/493,858 filed Jun. 6, 2011 hereby incorporated by reference.

TECHNICAL FIELD

One or more embodiments of the present invention relate to the field of Optical Coherence Tomography (OCT). In particular, the invention described herein provides systems and methods for achieving efficient matching of spectral and power characteristic of the source reference light in balanced detection using both hardware (optics) and electronic based solutions.

BACKGROUND

The sensitivity advantage of Fourier-domain optical coherence tomography (OCT) over time-domain OCT is well established (see for example Choma et al. "Sensitivity advantage of swept source and Fourier domain optical coherence tomography," Opt. Express 11, 2183-2189 (2003) and Leitgeb et al. "Performance of Fourier domain vs. time domain optical coherence tomography," Opt. Express 11, 889-894 (2003)). Spectral-domain OCT (SD-OCT) and swept-source OCT (SS-OCT also referred to as time-encoded frequency domain OCT or optical frequency domain imaging) are the two most commonly used Fourier-domain OCT architectures While there are many advantages of SS-OCT over SD-OCT, including less vulnerability to fringe wash-out and better roll-off sensitivity among others, SS-OCT systems with laser sources with high relative intensity noise (RIN) may not provide shot-noise limited performance like SD-OCT systems (see for example Yun et al. "High-speed optical frequency domain imaging," Opt. Express, 11 2953-2963 (2003) and Yun et al. "High-speed spectral-domain optical coherence tomography at 1.3 µm wavelength," Opt. Express 11, 3598-3604 (2003)). Typical experimental measurements of swept-source systems with lasers exhibiting RIN of ~120 dB/Hz show sensitivity performance that is 10-12 dB less than theoretical shot-noise limited sensitivity. Incomplete RIN suppression might be one of the most significant factors for the reduced sensitivity performance in SS-OCT systems. A solution aimed towards increasing the sensitivity of SS-OCT systems could be one of the decisive factors for choosing SS-OCT system architecture for future OCT systems.

Figure 1:
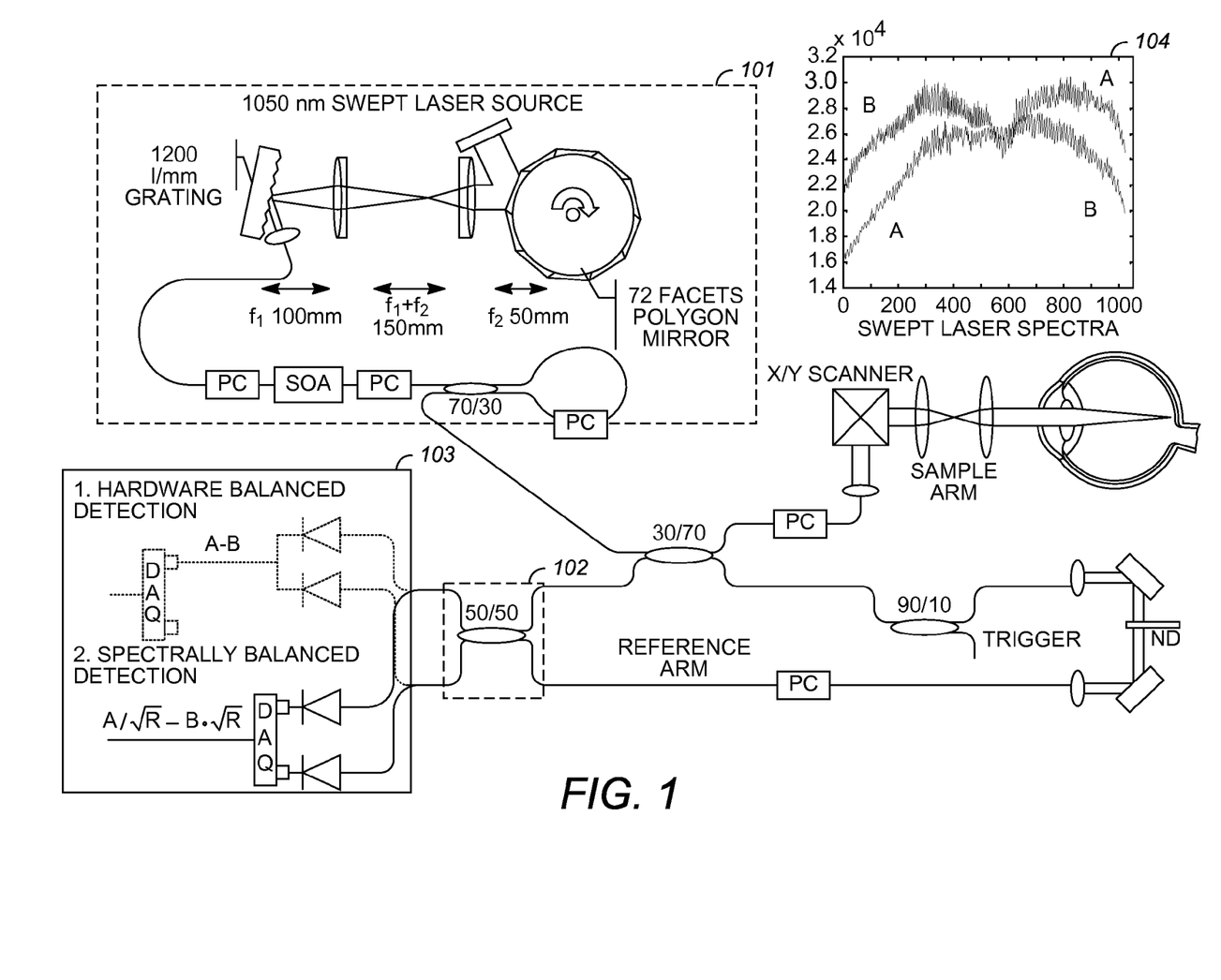
FIG. 1 shows a prior art SS-OCT employing two types of balanced detection schemes resulting in reduced RIN noise suppression.

Chen et al. identified the non-uniform wavelength dependent splitting ratios of fiber optic couplers as the primary source of incomplete RIN suppression and proposed one means to reduce RIN suppression in an SS-OCT system (Chen et al. "Spectrally balanced detection for optical frequency domain imaging," Opt. Express 15, 16390-16399 (2007)). The system employed by Chen et al. is shown in FIG. 1. As will be described below, the figure illustrates two different detection schemes, a conventional or standard hardware based balanced detection method (single channel data output) and their improved spectrally balanced detection scheme (dual-channel data output) that results in improved RIN noise suppression.

The box 101 in the top left corner of FIG. 1 shows the swept-laser source, in this case realized by using a rotating polygon minor based optical filter and semiconductor optical amplifier SOA. The light or radiation is divided into reference and sample arms at a 70/30 fiber coupler. The sample arm is directed to a slit lamp with an integrated X/Y scanner that scans the light over a sample of interest. The returned light from the sample is recombined with the source reference light at a 50/50 fiber optic coupler 102 and the resulting interference signal is divided into two output ports which can be used for either single-channel acquisition hardware balanced detection or dual-channel acquisition spectral balanced detection. Balanced detection is typically used in TD-OCT and SS-OCT to reduce RIN noise and fixed pattern noise artifacts (FPN). Fixed pattern noise may arise due to ripple modulations in the source spectral sweep. In a conventional SS-OCT balanced detection scheme (shown in dotted lines in the bottom left box 103 and labeled "1. Hardware balanced detection"), the two outputs from the 50/50 coupler are directed to the two input ports of a balanced detector.

Figure 2:
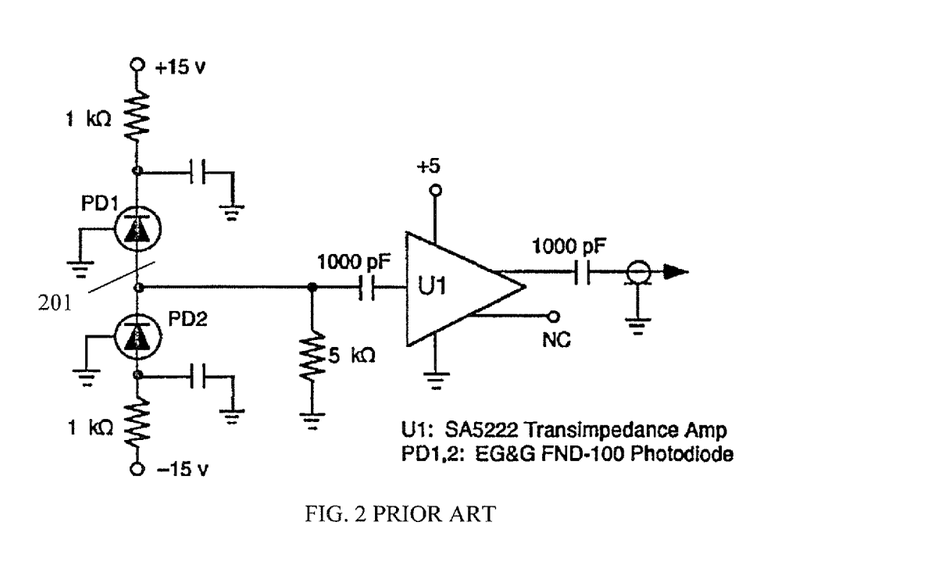
FIG. 2 illustrates the general elements of a typical balanced detection scheme.

A typical balanced detector consists of two reverse-biased photodiodes realized by applying voltages of same amplitude but opposite polarity as shown in FIG. 2 (see for example Houser et al. "Balanced detection technique to measure small changes in transmission," Applied Optics, 33 1059-1062 (1994)). The light incident on each of the photodiodes PD1 and PD2 generates photocurrents which are subtracted from each other at the junction 201 of the two photodiodes. The subtracted current signal is then converted to a voltage by a transimpedance amplifier U1. In the case of SS-OCT and TD-OCT, balanced detection results in addition of the interference signals while the DC component (due to source reference light), and hence the RIN noise, is subtracted and nullified.

To achieve optimized balanced detection with the least amount of RIN noise and FPN artifacts, a uniform splitting ratio over the whole spectral sweep of laser is necessary. However, as box 104 inset in the upper right hand corner of FIG. 1 illustrates for the signal measured at each detector of the balanced detector individually A and B, the splitting ratios of fiber optic couplers vary with wavelength. Chen et al. found that the wavelength dependent splitting ratio deviated by ±12% over a wavelength range of 60 nm. Chen's proposed detection scheme, shown in solid lines in the bottom left hand box 103 of FIG. 1 (and labeled "2. Spectrally balanced detection"), involves directing the divided reference signal to two detectors and digitizing the electrical signals separately. The balanced detection in this scheme is performed in the digital domain with an optimized balancing algorithm. The ratio of the two channels was measured and a compensation function was calculated to describe the channel ratio according to: $R(\lambda)=(S_{ch1}(\lambda)/S_{ch2}(\lambda))$. The balanced detection was then performed by rescaling the output from two detectors and subtracting one from another according to:

$$S_{bal}=S_{ch1}(\lambda)/\sqrt{R(\lambda)}-S_{ch2}(\lambda)\cdot\sqrt{R(\lambda)}. \quad (1)$$

Moon et al. suggested an approach similar to Chen et al. where they used multi-channel acquisition (up to three channels) and corrected the signal in digital domain after applying various normalization schemes. (Moon et al. "Normalization detection scheme for high-speed optical frequency-domain imaging and reflectometry," Opt. Express 15, 15129-15146 (2007)).

While reducing RIN noise, these methods have several drawbacks including the requirement for twice the data bandwidth (dual channel detection), additional computation load for post processing, higher detector noise coming from the addition of multiple detectors and the requirement of higher bit-depth for each channel due to DC offset. Although introducing the need for dual channel detection, these methods only sample a single interferometer path.

Electronic methods of balancing an optically unbalanced signal prior to digitization have been shown (For example See U.S. Pat. No. 5,134,276 and corresponding product Nirvana™ (Newport Corporation)). This technique can be thought of as an analog calculation of a correction parameter applied to one of the photodiode currents prior to subtraction at the node and digitization. US Publication No. 2011/0228280 also describes methods of electronically balancing a single interferometer.

In light of the limitations of the prior art, here we describe both optical hardware and electronic based solutions to spectrally filter and attenuate the source reference light in optical coherence tomography in an effort to reduce RIN and FPN noise in OCT systems. For optical hardware based solutions, the means for spectral balancing can be located in the interferometer itself, or in one of the paths directing light to the balanced detection input ports, or in both locations to optimize matching of spectral and power characteristics of the source reference light prior to balanced detection (i.e. prior to electric signal current generation at the photodiodes and data acquisition). In addition to the optical hardware means, we present some new electronic balanced detection schemes in which the current generated by at least one of the photodiodes is divided or amplified dynamically to nullify the signal current due to unbalanced source reference light at the subtraction node of the modified balanced detector. Such designs can compensate for the non-uniform wavelength dependent splitting ratio of fiber optic couplers in SS-OCT systems. The majority of noise in an OCT system arises from the reference light as it is typically orders of magnitude larger than the sample light. Improved spectral matching of the source reference light in the two input arms of the balanced detector results in efficient FPN suppression and can increase the sensitivity of SS-OCT systems closer to shot-noise limited performance. The systems and methods described herein have the advantage of using half the data bandwidth, allowing for single channel detection and higher dynamic range (hence less bit-depth), and requiring no post-processing steps for RIN suppression compared to the solutions provided in the past.

SUMMARY

The invention described herein presents several embodiments of OCT system designs and modified balanced detection schemes providing hardware (optics) and electronic based solutions to achieve efficient matching of spectral and power characteristics of the source reference light in balanced detection. In one case, the efficient matching is made possible by spectrally filtering and attenuating the source reference light in the interferometer itself, or in one or both of the arms directing light to the balanced detection input ports, or a combination of the two. In a second case, the current generated by at least one of the photodiodes in the balanced detector is designed to nullify the current signal resulting from unbalanced reference lights in the two arms of the balanced detector. The time varying splitting or amplification ratio can be realized using a predetermined voltage waveform input. A novel application to electronic balanced detection schemes in which a single source noise reference detection is balanced against the interferometric signals from multiple interferometers is also presented. Such a design may efficiently provide balanced detection for a parallel sampling OCT configuration.

While the embodiments described herein apply to SS-OCT, the invention could be used in any balanced detection interferometric system. The concepts described herein can apply to two different types of OCT system designs with balanced detection: the type shown in FIG. 1 in which the interference signal, resulting due to overlap of the sample and reference light, is divided into two channels for balanced detection or a type in which input to one port of the balanced detector has the interference signal and the input to other port has only the light from the reference source.

Compared to the methods used by Chen et al. and Moon et al., the subject invention uses single channel detection (cost effective for data acquisition and leads to reduction in overall detector noise), provides higher dynamic range due to elimination of DC component and RIN noise prior to amplification (allowing the use of smaller bit-depth for acquisition) and eliminates the need for post-processing correction of the data for improved RIN suppression. It is estimated that a 6 dB sensitivity improvement could be realized on the existing state-of-the-art SS-OCT systems by implementing the proposed spectrally balanced detection.

DETAILED DESCRIPTION

Included herein are several design ideas for fiber-optic, bulk-optic and hybrid fiber-optic-bulk optic SS-OCT systems which can be used to achieve spectral balance of source reference light using a single channel of balanced output. Although the ideas presented are specific to SS-OCT, similar ideas for balancing the spectral characteristics can also be applied to time-domain (TD-OCT) and spectral domain (SD-OCT) OCT systems.

Figure 3:
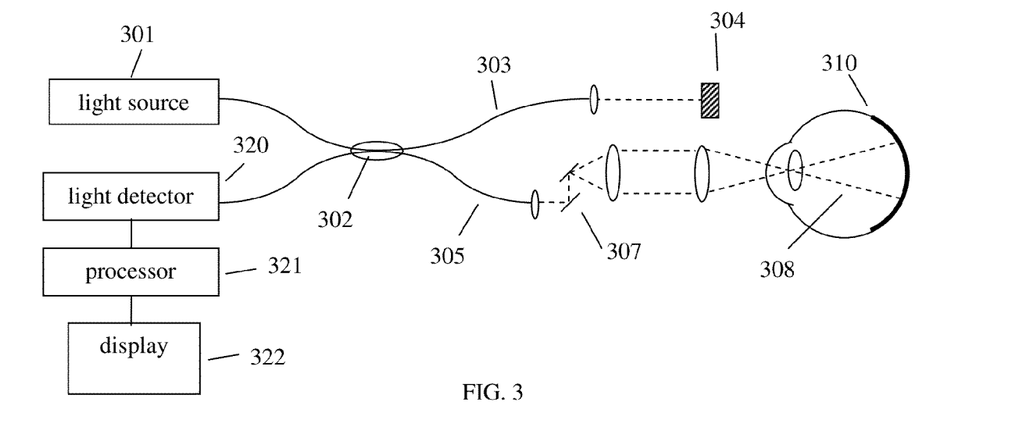
FIG. 3 shows the basic components of an OCT system.

As shown in FIG. 3, an OCT system typically includes a light source, 301. For SS-OCT this source is a swept wavelength source. Light from source 301 is routed, typically by optical fiber 305, to illuminate the sample 310, a typical sample being tissues in the human eye. The light is scanned, typically with a scanner 307 between the output of the fiber and the sample, so that the beam of light (dashed line 308) is scanned laterally (in x and y) over the area or volume to be imaged. Light scattered from the sample is collected, typically into the same fiber 305 used to route the light for sample illumination. Reference light derived from the same source 301 travels a separate path, in this case involving fiber 303 and retro-reflector 304 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 302, to form light interference in a detector 320. Although a single fiber port is shown going to the detector, those skilled in the art recognize that various designs of interferometers can be used for balanced or unbalanced detection of the interference signal. The output from the detector is supplied to a processor 321. The results can be stored in the processor 321 or displayed on display 322.

The Fourier transform of the interference light reveals the profile of scattering intensities at different path lengths, and therefore scattering as a function of depth (z-direction) in the sample (see for example Leitgeb et al. "Ultrahigh resolution Fourier domain optical coherence tomography," Optics Express 12(10):2156 2004). The profile of scattering as a function of depth is called an axial scan (A-scan). A set of A-scans measured at neighboring locations in the sample produces a cross-sectional image (tomogram or B-scan) of the sample. A collection of B-scans makes up a data cube or cube scan.

The Interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. While various embodiments are described below, one skilled in the art could imagine additional embodiments that would achieve these goals falling within the scope of the invention. One aspect of the present invention is the introduction of some optical hardware elements to counter act or compensate for the spectral variation in the transmission of the fiber coupler used to separate the components for balanced detection, allowing for reduced noise and a single channel of digital balanced output.

The embodiments described below are envisioned for the field of ophthalmology so an eye is shown as the sample. However, the methods could be applied to any sample and for other fields of medical imaging such as intravascular OCT, etc. The inventive concepts can be applied to any laser source capable of producing sweeping wavelength (or time encoded frequency) radiation either by filtering or successive frequency stepping, including semiconductor optical amplifier (SOA) based systems and Fourier domain mode locked lasers (FDML) among others.

Figure 4:
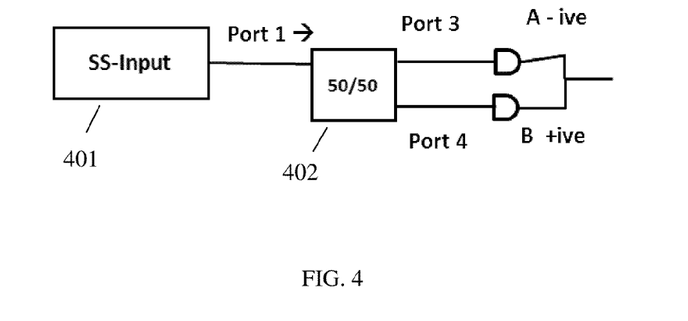
FIG. 4 illustrates an experimental set-up for measuring the wavelength dependent splitting of fiber optic couplers.

Before describing the different designs to achieve efficient RIN and FPN suppression, it is helpful to appreciate the incomplete RIN suppression demonstrated with current state-of-the-art systems. In a 'classical' SS-OCT system as shown in FIG. 1 with hardware balanced detection (labeled "1.Hardware balanced detection" in the bottom left box 103 of FIG. 1 shown in dotted lines), the source reference light incident on the 50/50 fiber optic coupler is divided into two arms and fed into the two ports of the balanced detection system. The fiber optic coupler has a wavelength dependent splitting ratio, hence it is not possible to balance the power in the two arms throughout the spectrum or 'sweep' of the swept-source. The splitting ratio as a function of wavelength for a broadband 50/50 coupler from AC photonics can be characterized using a set-up shown in FIG. 4. The light from the swept source SS-input 401 is fed into port 1 of the fiber optic coupler 402 (AC photonics, 50/50) and the resulting light outputs are recorded at Port 3 (same-port transmission) and Port 4 (cross-port transmission). The resulting signals A and B are measured at the two detectors of a balanced detection scheme. First, the light outputs in the two arms of the coupler are measured separately by feeding each port individually into the balanced detector with the other port disconnected, and then both ports are connected to the balanced detector at the same time to get the single channel differential output.

Figure 5:
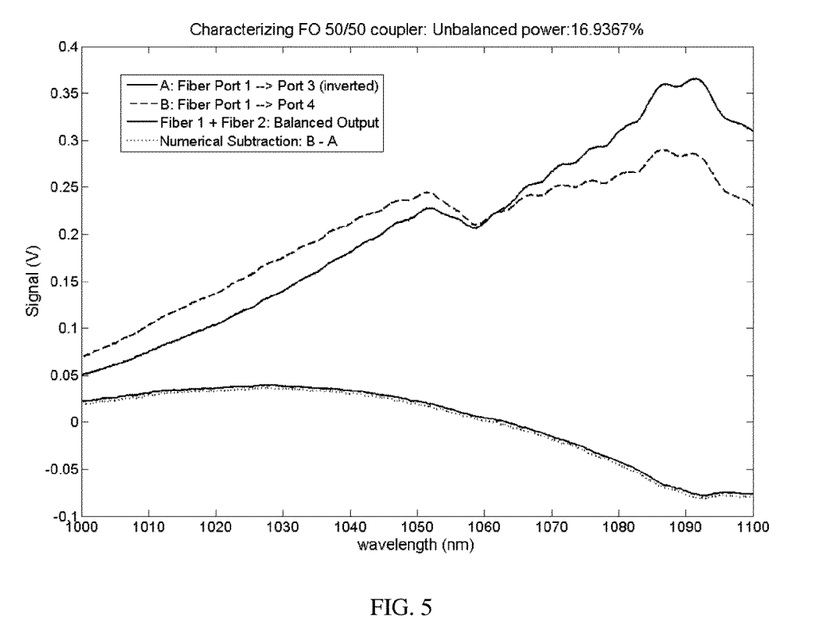
FIG. 5 shows a plot of output voltage vs. wavelength for a series of measurements obtained using the experimental set-up illustrated in FIG. 4.

The plot of the raw output voltage vs. wavelength for the different measurements is shown in FIG. 5. The top two traces A and B show the signal measured on each detector individually, each of which varies with wavelength. The bottom trace representing the resulting balanced output Fiber 1+Fiber 2, which would ideally be straight, shows a variation across the wavelengths. The unbalanced power was calculated according to the equation below to verify the performance of the balanced detector:

$$Unbalaced\ Power(\%) = 100 \times \int_{\lambda=1000nm}^{\lambda=1100nm} \frac{|P_3(\lambda) - P_4(\lambda)|}{(P_3(\lambda) + P_4(\lambda))/2} d\lambda. \quad (2)$$

Figure 6:
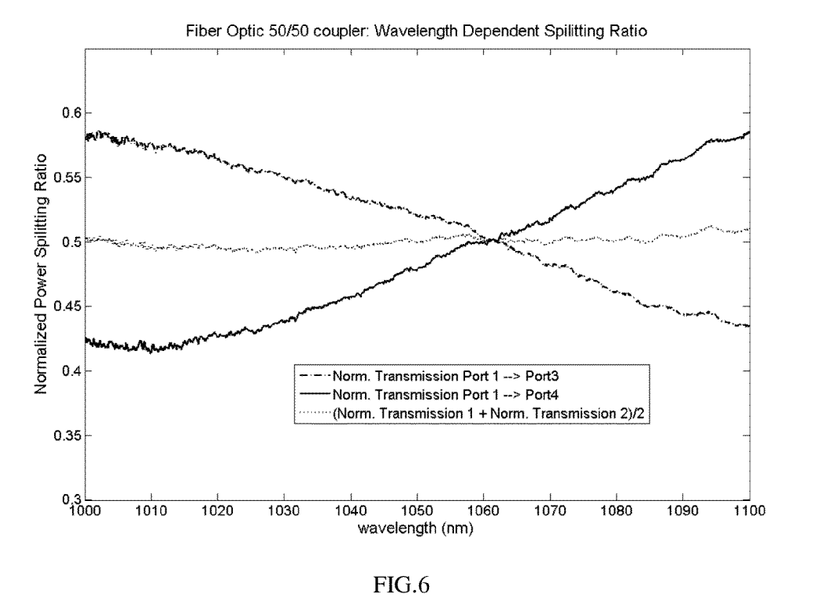
FIG. 6 shows the normalized wavelength dependent splitting ratio of a fiber optic coupler.

FIG. 6 shows the normalized wavelength dependent splitting ratio of the 50/50 coupler. The figure illustrates that the same-port and cross-port transmissions vary with wavelength in the opposite directions, such that over the entire wavelength band if the two measurements were added together and normalized, a relatively constant splitting ratio can be realized. While this is done by a calculation here, the goal of the hardware designs presented herein is to add optical elements that compensate for the wavelength dependent splitting and cancel out this wavelength dependence. In the measurements reported here, the unbalanced power exhibited a typical range of 16-18% for different couplers of the same manufacturer (AC photonics). The slopes of the splitting ratios were similar in two couplers and ranged from 0.16-0.18%/nm. It can be seen from the initial characterization experiments that the unbalanced power is quite significant for a standard fiber-optic coupler (16-18%) and is the most likely reason for incomplete RIN suppression.

Hardware (Optics) Based Improved Balanced Detection

The invention described herein is described using several OCT system designs in which the unbalanced power is minimized and hence RIN/FPN suppression is optimized. The basic approach is to spectrally filter and attenuate the source reference light in the interferometer itself, or in one or both of the arms directing light to the balanced detection input ports, or a combination of these two approaches to optimize the matching of the spectral and power characteristics of the source reference light prior to balanced detection.

Spectral shaping and power attenuation described in the various embodiments of the invention can be achieved in number of ways. Optical elements and sub-systems which can be used for spectral filtering include:

1. Fiber optic couplers: The wavelength dependent transmission functions of fiber optic couplers can be used to achieve spectral balancing, effectively countering out the negative impact that the splitting coupler has on the system.
2. Dielectric coatings on the mirrors in reference arm, such that the reflection has a wavelength dependence, can be used for spectral balancing.
3. Coating the fiber connector tips to achieve desired spectral filtering.
4. Chromatic aberrations in the lens in reference arm and imperfect collection of light by the fiber can also be used as a sub-system for spectral shaping.
5. Any optical component in one of the arms or reference arm which has some transmission dependence on the wavelength can be used as a spectral shaping element (i.e. filters or a bulk beam splitter used in interferometer or as an extra component in reference arm).
6. Use of any bulk optic or fiber optic spectral shaping sub-systems can also be used for spectral filtering.

Hence spectral filtering and power attenuation achieved by using individual or combinations of the elements above are all possible embodiments of this invention. Several specific embodiments of the invention will be described in detail below.

Figure 7:
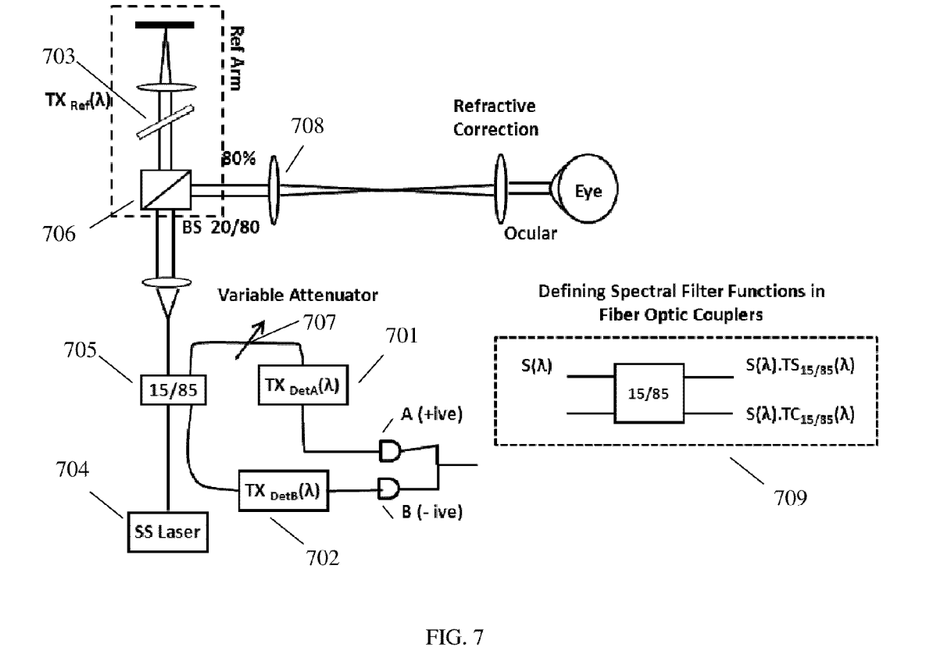
FIG. 7 shows one embodiment of the present invention for a hybrid fiber-bulk optic interferometer design capable of spectral balancing for improved RIN and FPN noise suppression in which one arm of the balanced detector consists of only source reference light.

One of the implementations of such design for a hybrid fiber-optic bulk-optic interferometer design is shown in FIG. 7. In this design spectral filters $TX_{detA}(\lambda)$ 701 and $TX_{detB}(\lambda)$ 702 are utilized in each arm of the balanced detection set-up to optimize the matching of the spectral characteristics of the light prior to detection. An additional filter $TX_{ref}(\lambda)$ 703 is included in the reference arm to further optimize the matching. Light from a source 704 is split using a 15/85 fiber coupler 705. The same port transmission passes to the interferometer and the cross port transmission containing only source reference light is directed towards detector A in a balanced detection scheme. The sample and reference are split and are recombined in free space at an 80/20 beamsplitter 706 and the resulting interference signal and reference source light is directed to the 15/85 fiber coupler 705 where it is split and the cross port transmission is directed to detector B of the balanced detector. A variable attenuator 707 is shown in the path to detector A to achieve power balance. While this embodiment shows multiple spectral filters and a variable attenuator, it is conceivable that a single optical element could achieve both functions as will be shown in a later embodiment of the invention. A 15/85 coupler 705 was chosen to optimize collection of sample light but the methods would apply to any coupling ratio selected for a particular interferometer system. A scanner (not shown) for scanning the beam is positioned behind lens 708 for scanning the beam across multiple transverse locations on the sample.

The inset 709 of FIG. 7 provides an illustrative definition of the spectrally varying transmission functions for the 15/85 coupler 705. $TC_{15/85}(\lambda)$ and $TS_{15/85}(\lambda)$ are the cross-port and same-port transmission functions of the fiber optic coupler respectively. If $S(\lambda)$ is the source reference power, the reference light incident on detector ports A and B of the balanced detector can be written as (ignoring coupler losses and coupling efficiency):

$$I_{A(+ive)}(\lambda) = \eta_A \cdot S(\lambda) \cdot TC_{15/85}(\lambda) \cdot TX_{DetA}(\lambda)$$

$$I_{B(-ive)}(\lambda) = \eta_{Ref} \cdot S(\lambda) \cdot TS_{15/85}(\lambda) \cdot TX_{Ref}(\lambda) \cdot TC_{15/85}(\lambda) \cdot TX_{DetB}(\lambda). \quad (3)$$

Here $\eta_A$ is the attenuation caused by the variable optical attenuator, $\eta_{Ref}$ is the attenuation of the reference source light caused by the interferometer, $TC_{15/85}(\lambda)$ and $TS_{15/85}(\lambda)$ are the cross-port and same-port transmission functions of the fiber optic coupler, respectively. $TX_{Ref}(\lambda)$ is the spectral filter function of the interferometer for the source reference light, and $TX_{DetA}(\lambda)$ and $TX_{DetB}(\lambda)$ are the spectral transmission functions of an optical component, or optical sub-system in the two arms going to the input ports of the balanced detector. By choice or design of the appropriate spectral filters, one can match the power and spectral characteristics of the incident source reference light at the two ports of the balanced detector by satisfying the following condition:

$$\eta_A \cdot TX_{DetA}(\lambda) = \eta_{Ref} \cdot TS_{15/85}(\lambda) \cdot TX_{Ref}(\lambda) \cdot TX_{DetB}(\lambda). \quad (4)$$

The spectral filters are designed to have spectral transmissions that compensate for the spectral dependence of the coupler splitting that was illustrated in FIGS. 5 and 6. Note that the equations include only the source reference light. As previously mentioned, the reference light is typically orders of magnitude larger than the reflected sample light so is the largest contributor to noise in the measurements. In the balanced detection set-up shown in FIG. 7, different from the case of FIG. 1, one port of the balanced detector consists only of reference light split off from the 15/85 fiber coupler 705, not interference signal. The methods described herein apply equivalently to both cases of balanced detection.

Figure 8:
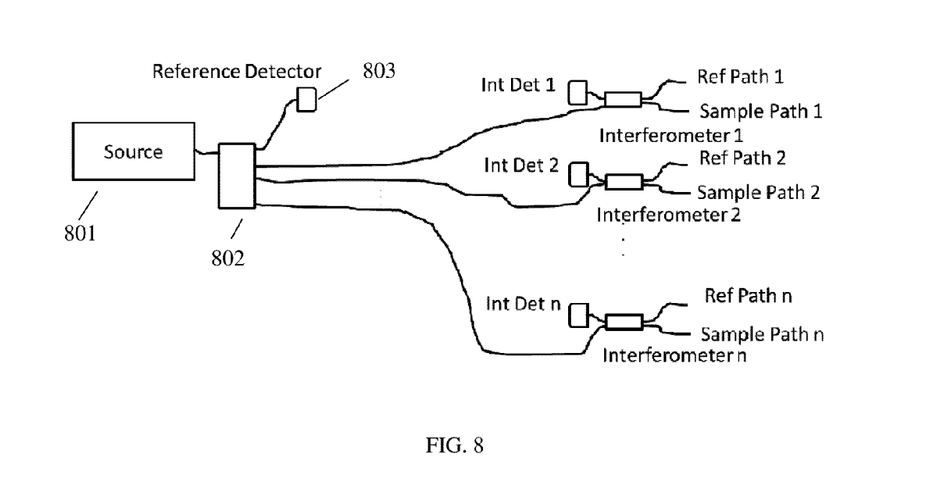
FIG. 8 shows a further embodiment of the invention in which a design using solely source reference light can be combined with multiple interferometers for imaging multiple sample locations in parallel.

One advantage of a system design in which the balanced detector includes one port that consists only of reference light, is that the reference signal may be simultaneously balanced against multiple channels, each of which contains a different interference signal, without a need for duplicate measurements of the reference light for the purpose of balancing. An example of this is shown in FIG. 8 in which signal from a source 801 is split into multiple parts by a splitter or coupling element 802. One of the portions is directed to a reference detector which can serve as one detector 803 in n balanced detection schemes. The other n portions are directed to separate interferometers, each of which has its own detector Int Det 1, Int Det 2, Int Det n, for collecting the interference light for each interferometer which can each be used as a second detector in balanced detection measurements. Additional embodiments in which the reference arm is divided and detected differently can be envisioned by those skilled in the art. Whether the balanced detection is realized digitally or in using analog subtraction would depend on the number of interferometers. This multiple interferometer system could be used with or without the spectral balancing techniques described herein. For the embodiment illustrated in FIG. 8, a spectral filter could be inserted before the reference detector to optimize the balanced detection and account for wavelength dependent splitting of the coupling in the system. Such a system may be used for parallel measurements, for example enabling greater Maximum Permissible Exposure on the eye by dividing the measurement beam to multiple eye locations or for measuring multiple depth locations in the sample simultaneously. These multiple depth locations could both be in the anterior or posterior segments or one could be from the anterior segment and one could be from the posterior segment.

Figure 9:
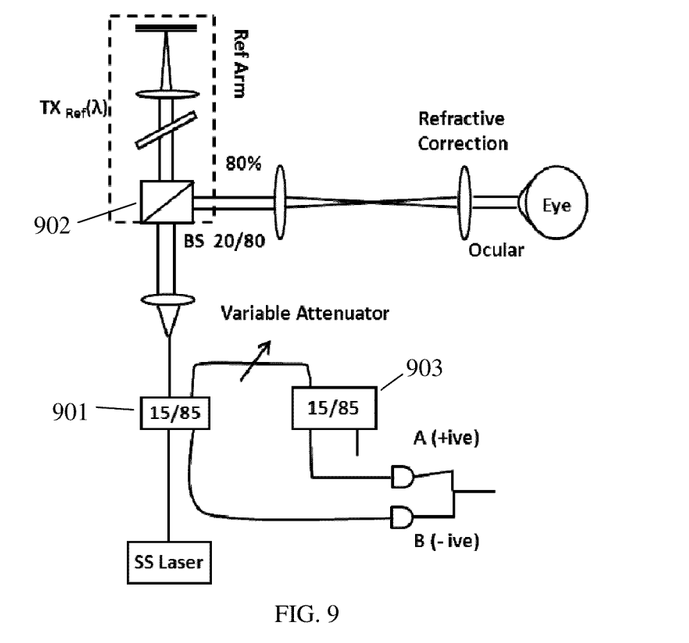
FIG. 9 shows an embodiment of the invention in which spectral balancing is achieved using a fiber coupler in one of the input arms to the balanced detector.

FIG. 9 shows another embodiment of the invention where a 15/85 fiber optic coupler 901 is used in one of the input arms of the balanced detection system to compensate for non-uniform spectral characteristics of the light at the two inputs of a balanced detector. Like FIG. 7, the sample and reference beams are overlapped at a 20/80 beamsplitter 902 in free space and the two arms leading to the balanced detector are generated from a 15/85 fiber coupler 901, leading to only reference light in the path leading to port A of the balanced detector. In this case, the spectral dependence of the 15/85 coupler 901 is balanced by using the opposite transmission paths (cross-path instead of same-port) of another 15/85 coupler 903 in the path leading to port A of the balanced detector. The reference light incident on detector ports A and B of the balanced detector for the schematic shown in FIG. 9 can be written as:

$$I_{A(+ive)}(\lambda) = \eta_A \cdot S(\lambda) \cdot TC_{15/85}(\lambda) \cdot TS_{15/85}(\lambda)$$

$$I_{B(-ive)}(\lambda) = \eta_{Ref} \cdot S(\lambda) \cdot TS_{15/85}(\lambda) \cdot (BST_{20/80}(\lambda))^2 \cdot TC_{15/85}(\lambda). \quad (5)$$

For a given polarization of source reference light, the spectral transmission function of the cube beamsplitter responsible for splitting the signal and reference paths (BS 20/80 706 in FIG. 7 and 902 in FIG. 9) ($(BST_{20/80}(\lambda))^2 \sim K$) can be assumed to be fairly uniform over the wavelength range, and hence the spectral characteristics of the reference light in the two arms can be closely matched by adjusting the uniform power attenuation in one of the arms such that:

$$\frac{I_{A(+ive)}(\lambda)}{I_{B(-ive)}(\lambda)} = \frac{\eta_A}{\eta_{Ref} \cdot K} = C_1 \approx 1. \quad (6)$$

Slight modifications can be made in the designs shown in FIGS. 7 and 9 to allow switching between imaging in the anterior and posterior sections of the eye such as adding a variable delay path in one of the arms and adding or removing optics to adjust the focusing properties of the beam on the sample. Such modifications or changes in the design would still be within the scope of this invention.

Figure 10:
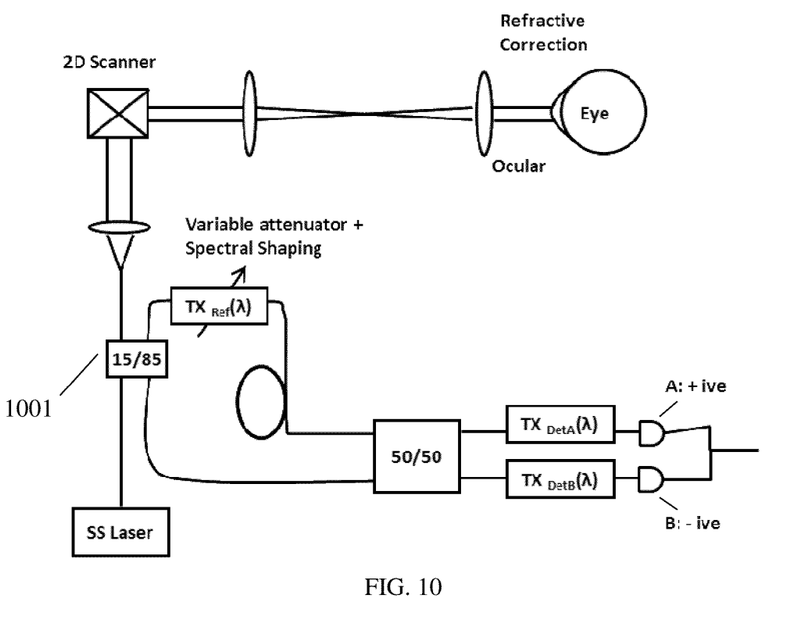
FIG. 10 shows an embodiment of the invention applied to a fiber optic based interferometer design in a Mach-Zehnder interferometer with a transmissive reference arm.
Figure 11:
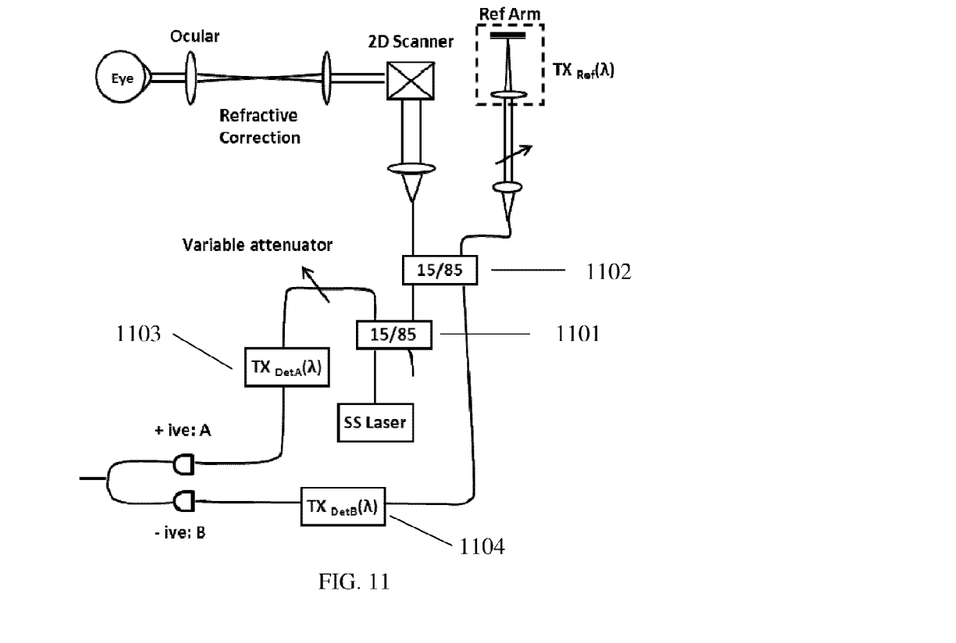
FIG. 11 shows an additional embodiment of the invention applied to a fiber optic based interferometer design.

There are several other SS-OCT designs embodying the invention to realize spectral and power matching for enhanced sensitivity and RIN noise suppression. FIGS. 10 and 11 show two possible embodiments of spectral balancing in fiber optic based SS-OCT systems. The embodiment shown in FIG. 10 is based on a transmissive reference arm (Mach-Zehnder interferometer) and utilizes spectral and power filtering in the reference arm and spectral filtering in each arm leading to the balanced detector. The reflected sample light is combined with the source reference light at the 15/85 fiber coupler 1001. Like the system in FIG. 1, both arms of the balanced detection set-up contain interference light between the signal and reference. FIG. 11 shows an embodiment utilizing two 15/85 fiber couplers 1101, 1102 and spectral filters 1103, 1104 in the two arms leading to the balanced detector A, B.

Figure 12:
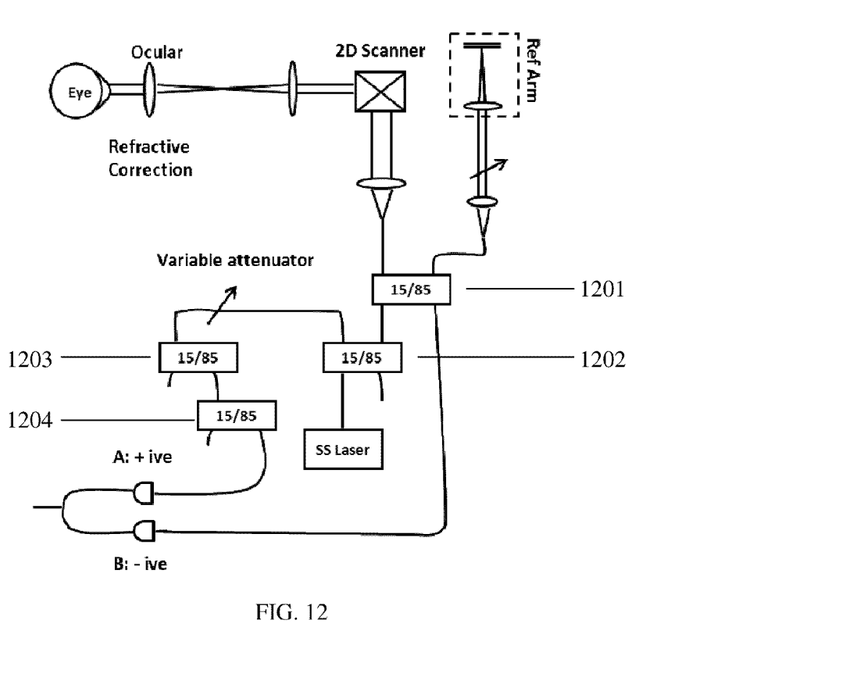
FIG. 12 shows an embodiment of the present invention in which a cascade of fiber optic couplers is used to achieve spectral and power balancing in a balanced detection set-up.

It is noted that while the designs shown in FIGS. 10 and 11 use three spectral shaping elements or sub-systems ($TX_{Ref}(\lambda)$, $TX_{DetA}(\lambda)$, and $TX_{DetA}(\lambda)$), designs in which fewer spectral shaping elements are also possible. FIG. 12 shows an additional embodiment of the invention in which spectral balance is achieved by using a cascade of 15/85 fiber optic couplers 1201, 1202, 1203, and 1204. As previously mentioned, specific coupling ratios are used for illustrative purposes only and the invention described herein applies to additional coupling ratios that could be used to achieve interferometer designs with improved balanced detection.

Assuming that no spectral shaping occurs in the reference arm, the source reference light incident of detector ports A and B of the balanced detector for the schematic shown in FIG. 12 can be written as:

$$I_{A(+ive)}(\lambda) = \eta_A \cdot S(\lambda) \cdot TS_{15/85}(\lambda) \cdot (TC_{15/85}(\lambda))^2$$

$$I_{B(-ive)}(\lambda) = \eta_{Ref} \cdot S(\lambda) \cdot (TC_{15/85}(\lambda))^2 \cdot TS_{15/85}(\lambda). \quad (7)$$

It can be seen from this equation that spectral balancing has been achieved if the transfer functions of the different couplers are the same.

Figure 13:
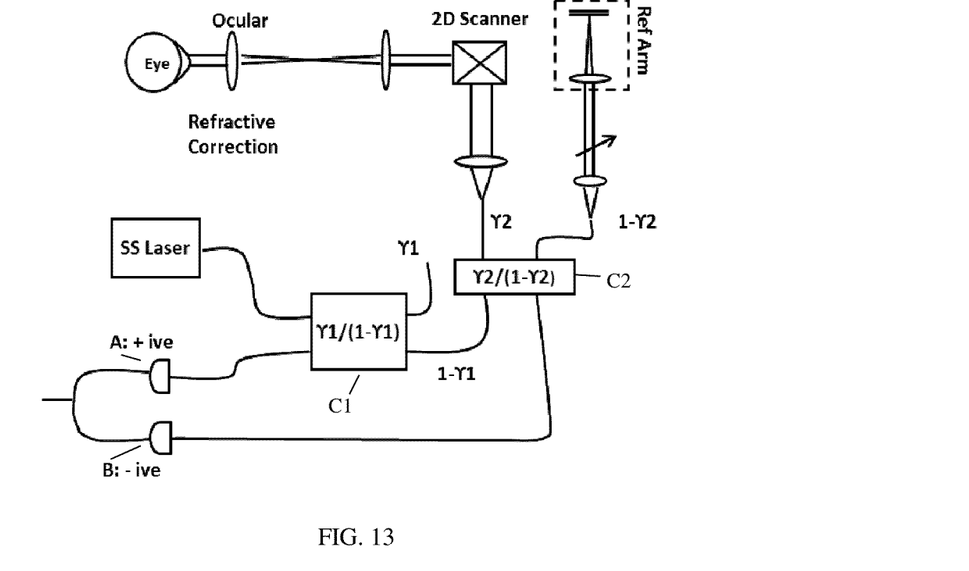
FIG. 13 illustrates a preferred embodiment of the present invention in which a two coupler based Michelson interferometer design is optimized for spectral and power balancing based on the splitting ratios of the couplers.

FIG. 13 illustrates a preferred embodiment of the present invention in which a two coupler based Michelson interferometer design is used to realize spectral and power matching for enhanced sensitivity and RIN noise suppression in a SS-OCT system. The two couplers designated C1 and C2 in FIG. 13 have coupling ratios that are designed to optimize balanced detection as will be described in detail below. Although an interferometer with a similar layout of fiber optic couplers has been used before for time-domain OCT (see for example Drexler et al. "In vivo ultrahigh-resolution optical coherence tomography," Opt. Lett., 24, pp 1221-1223 (1999)), the designs in the prior art were not optimized for balanced detection. The interferometer design used by Drexler et al. used a 50/50 coupler splitting ratio for C2 that would typically result in unbalanced power outputs at the balanced detector. The imbalance of power at the balanced detector input ports could be minimized if only a very small fraction (~1-4%) of the laser power is directed to the sample arm. However, typical broadband light sources have limited optical powers, and hence it is critical to modify the design for minimizing unbalanced power in the detection end.

In U.S. Pat. No. 6,927,860, Podoleanu et al. describe optimizing splitting ratios to maximize sensitivity performance of the system, but used a Mach-Zehnder interferometer with a transmissive optical delay configuration and used a 50/50 coupler at the balanced detection end. Izatt et al. had also suggested several interferometer designs for optimized balanced detection, but their designs included a directional component such as optical circulator and they also used a 50/50 coupler at the balanced detection end (see for example, Rollins et al. "Optimal interferometer designs for optical coherence tomography," Opt. Lett. 24, pp 1484-1486 (1999)). In contrast to the prior art, this embodiment does not use any directional component and the output coupler splitting ratio is not limited to 50/50.

In the embodiment shown in FIG. 13, splitting ratios of the C1, C2 are chosen to optimize the balanced detection performance The key idea of this design is that the product of the coupling ratios of the two couplers should be such that the reference power in the two photodetectors should be equal for at least one wavelength in the central portion of the laser sweep. If coupler C1 and C2 have splitting ratios ($\gamma 1/(1-\gamma 1)$) and ($\gamma 2/(1-\gamma 2)$) respectively, then the product of the coupling ratio must satisfy the following condition: $(1-\gamma 2)*\gamma 1 = \gamma 2$. The performance of balanced detection could be improved further if the spectral shaping of the first coupler C1 can fully or partially compensate for the non-uniform wavelength dependent splitting ratio of the second coupler C2. In an alternative embodiment, the gain of the two photodetectors A, B of the balanced detector can be adjusted to compensate for the unequal reference power at the two ports of the balanced detector.

Electronics Based Improved Balanced Detection

We now present some new electronic balanced detection schemes in which the signal generated by at least one of the photodiodes is divided or amplified dynamically to nullify the signal current due to unbalanced source reference light at the subtraction node and a potential application of electronic balanced detection schemes. In these embodiments, the time varying splitting or amplification ratio can be provided by a predetermined voltage waveform input. Such a design can compensate for the non-uniform wavelength dependent splitting ratio of fiber optic couplers in SS-OCT systems.

A typical balanced detector consists of two reverse-biased photodiodes PD1 and PD2 realized by applying voltages of the same amplitudes but opposite polarity as shown in FIG. 2 (see for example Houser et al. "Balanced detection technique to measure small changes in transmission," Applied Optics, 33 1059-1062 (1994)). As described above, the light incident on each of the photodiodes generates photocurrents which are subtracted from each other at the junction of the two photodiodes 201. The subtracted current signal is then converted to a voltage by a transimpedance amplifier U1. In the case of SS-OCT and TD-OCT, balanced detection results in addition of the interference signals while the DC component (due to source reference light), and hence the RIN noise, is subtracted and nullified. However, as described previously, non-uniform wavelength dependent splitting ratios of fiber optic couplers or beam combiners result in unbalanced reference light and hence unbalanced signal, limiting the RIN noise suppression. The current due to unbalanced reference light incident on two photodiodes can be written as:

$$i_{RefUnbal}(\lambda) = i_{chA}(\lambda) - i_{chB}(\lambda) = \sigma \cdot S_{chA}(\lambda) - \sigma \cdot S_{chB}(\lambda) \quad (3)$$

Here $\sigma$ is the responsivity of the photodiodes, $i_{chA}$ and $i_{chB}$ the currents generated by the two photodiodes.

Figure 14:
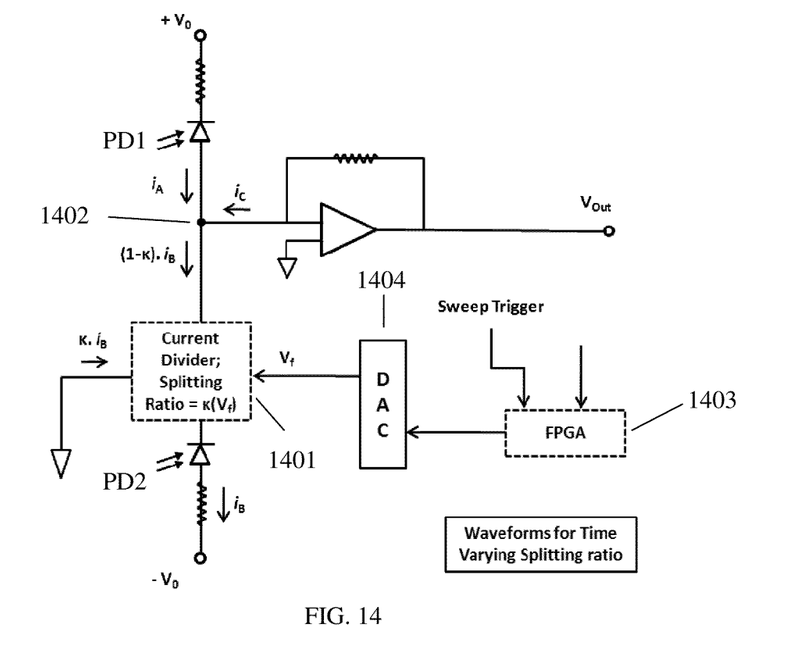
FIG. 14 illustrates a preferred embodiment of an electronic balancing technique to achieve spectral balance in a balanced detection set-up.

FIG. 14 shows one embodiment of the present invention in which the photocurrent generated by at least one of the photodiodes PD1, PD2 in a balanced detection set-up is dynamically divided wherein the dynamic splitting ratio during the wavelength sweep is established by a predetermined voltage output waveform. A current divider 1401 has a splitting ratio, $\kappa$, that is a function of the input voltage $V_f$, which is generated by a predetermined waveform based on the pre-calibrated knowledge about the channel ratio compensation function $R(\lambda)$. The time-varying splitting is largely determined by the non-uniform wavelength dependent splitting ratio of the fiber coupler prior to balanced detector. Hence the beam coupler could be calibrated to determine the wavelength dependent transmission in a way similar to the calibration shown in FIG. 6. The input voltage waveform to the current divider is synchronized with the sweeping action of the light source and is generated such that the current splitting ratio can be approximated as following: $\kappa(\lambda) = 1 - R(\lambda)$. The subtracted current at the junction of the two detectors 1401 can now be written as:

$$i_{Ref}(\lambda) = \sigma \cdot S_{chA}(\lambda) - \sigma \cdot (1 - \kappa) S_{chB}(\lambda) \quad (4)$$
$$= \sigma \cdot S_{chA}(\lambda) - \sigma \cdot \left(\frac{S_{chA}(\lambda)}{S_{chB}}\right) S_{chB}(\lambda).$$

For a given SS-OCT system, the compensation function can be measured by calibrating the channel ratio: $R(\lambda) = (S_{ch1}(\lambda)/S_{ch2}(\lambda))$. The current splitting ratio may have a non-linear dependence on input voltage $V_f$, however, the right waveform can be generated to get a wavelength dependent splitting ratio such that $\kappa(\lambda) = 1 - R(\lambda)$. FIG. 14 shows our preferred design to implement this concept. In our preferred embodiment, the pre-calibrated performance of the fiber optic coupler is used to generate the waveform shape. The waveform period is scaled to match with the sweep period, and the start of the sweep trigger can be used to trigger the waveform generation. The waveform generation is done by FPGA 1403, which could be converted into an analog signal ($V_f(\lambda)$) using a DAC 1404 and this analog voltage signal can be used as an input to produce time or wavelength varying splitting ratio ($\kappa(\lambda)$). Other implementations can also be used to realize the same invention including the use of other waveform generating circuits or components instead of FPGA 1403, and the use of an amplifier instead of a divider 1401 for the current.

A potential application of balanced detection schemes is to balance the output from multiple interferometers against a single reference signal containing only the source intensity and no interference signal analogous to the embodiment illustrated in FIG. 8 for optical hardware based balanced detection schemes. Such a design can provide a minimum number of optical detectors for a plurality of parallel detection channels, each of which is balanced to mitigate source noises. A digital subtraction method becomes more attractive as the number of sampled interferometers increases, as the overhead associated with digitizing the source signal is only paid once. In contrast, the optical hardware or analog subtraction hardware would typically be reproduced for each additional interferometer unless such additional interferometers are so similar that a single compensation be applied to all detection channels.

Although various applications and embodiments that incorporate the teachings of the present invention have been shown and described in detail herein, those skilled in the art can readily devise other varied embodiments that still incorporate these teachings.

The following references are hereby incorporated by reference:

US Patent Documents

U.S. Pat. No. 5,134,276 Hobbs "Noise cancelling circuitry for optical systems with signal dividing and combining means"

US Publication No. 2011/0228280 Schmitt et al. "Intensity noise reduction methods and apparatus for interferometric sensing and imaging systems"

U.S. Pat. No. 6,927,860 Podoleanu et al. "Optical mapping apparatus with optimized OCT configuration"

Non-Patent Literature

Chen et al. "Spectrally balanced detection for optical frequency domain imaging," Opt. Express 15, 16390-16399 (2007)

Choma et al. "Sensitivity advantage of swept source and Fourier domain optical coherence tomography," Opt. Express 11, 2183-2189 (2003)

Drexler et al. "In vivo ultrahigh-resolution optical coherence tomography," Opt. Lett., 24, pp 1221-1223 (1999)

Houser et al. "Balanced detection technique to measure small changes in transmission," Applied Optics, 33 1059-1062 (1994)

Leitgeb et al. "Performance of Fourier domain vs. time domain optical coherence tomography," Opt. Express 11, 889-894 (2003)

Leitgeb et al. "Ultrahigh resolution Fourier domain optical coherence tomography," Optics Express 12(10):2156 (2004)

Moon et al. "Normalization detection scheme for high-speed optical frequency-domain imaging and reflectometry," Opt. Express 15, 15129-15146 (2007)

Rollins et al. "Optimal interferometer designs for optical coherence tomography," Opt. Lett. 24, pp 1484-1486 (1999)

Yun et al. "High-speed optical frequency domain imaging," Opt. Express, 11 2953-2963 (2003)

Yun et al. "High-speed spectral-domain optical coherence tomography at 1.3 µm wavelength," Opt. Express 11, 3598-3604 (2003)

What is claimed is:

1. An optical coherence tomography (OCT) system, the system comprising:
   a light source arranged to generate a beam of radiation wherein the wavelength of the beam varies over time;
   a balanced detector with at least first and second photodetectors for acquiring data;
   at least one coupler functioning to direct a first portion of the beam to a sample and to direct a second portion of the beam to a reference arm, and for causing the light from the reference arm and the light reflected from the sample to be combined and for directing a portion of the combined light to the first photodetector and for directing a portion of one of the combined light, the source light, or light returning from the reference arm to the second photodetector and wherein the splitting ratio of the coupler varies as a function of the wavelength of the beam; and
   a means for compensating for the spectral dependence of the coupler to spectrally balance the light falling on the first and second photodetectors prior to data acquisition.

2. An OCT system as recited in claim 1, wherein at least one photodetector of the balanced detector does not receive combined light.

3. An OCT system as recited in claim 2, wherein the means for compensating for the spectral dependence of the coupler is located in the path leading to the photodetector that does not receive combined light.

4. An OCT system as recited in claim 1, wherein one photodetector receives light only from the source.

5. An OCT system as recited in claim 1, wherein the means for compensating for the spectral dependence of the coupler is located in at least one of the paths leading to the balanced detector.

6. An OCT system as recited in claim 1, wherein the means for compensating for the spectral dependence of the coupler is located within the reference arm.

7. An OCT system as recited in claim 1, wherein the means for compensating for the spectral dependence of the coupler is located in at least one of the paths leading to the balanced detector and in the reference arm.

8. An OCT system as recited in claim 1, wherein the means for compensating for the spectral dependence of the coupler comprises a spectral filter.

9. An OCT system as recited in claim 1, wherein the means for compensating for the spectral dependence of the coupler comprises a fiber coupler.

10. An OCT system as recited in claim 1, wherein the means for compensating for the spectral dependence of the coupler comprises multiple fiber couplers.

11. An OCT system as recited in claim 1, wherein the coupler and optics functioning to direct and combine light are fiber optics.

12. An OCT system as recited in claim 1, wherein the coupler and optics functioning to direct and combine light are a combination of bulk optics and fiber optics.

13. An OCT system as recited in claim 1, wherein the reference arm is a reflective reference arm.

14. An OCT system as recited in claim 1, wherein the directing and combining functioning is achieved using two couplers.

15. An optical coherence tomography (OCT) system, the system comprising:
   a light source for generating a beam of radiation that is swept in wavelength over time;
   a first, non-directional coupler having a first coupling ratio ($\gamma_1 /(1-\gamma_1)$) functioning to divide the beam into two portions of unequal optical powers where $\gamma$ is a power splitting fraction;
   a balanced detector with at least first and second photodetectors for acquiring data; and
   optical components functioning to direct the portion of the beam of lesser optical power from the first coupler to a second non-directional coupler having a second coupling ratio ($\gamma_2 /(1-\gamma_2)$) that divides the received portion of the beam into sample and reference arms and divides the light returning from the sample and reference arms into two portions of unequal optical powers, wherein one portion is directed back to the first coupler and the other portion is directed to the first photodetector and wherein the first coupler directs a portion of the reflected light to the second photodetector and wherein the coupling ratios of the two couplers satisfy the following condition $(1-\gamma_2)*\gamma_1=\gamma_2$ whereby the power from the reference arm supplied to both the first and second photodetectors is equal for at least one of the wavelengths in the central portion of the wavelength sweep.

16. An OCT system as recited in claim 15 wherein the spectral shaping of the first coupler is configured to compensate for the non-uniform wavelength dependent splitting ratio of the second coupler.

17. An optical coherence tomography (OCT) system, said OCT system comprising:
   a light source arranged to generate a beam of radiation wherein the wavelength of the beam varies over time;
   a beam divider for separating the beam along a sample arm and a reference arm, wherein the splitting ratio of the divider varies as a function of the wavelength of the beam;
   a detector for measuring radiation returning from both the sample arm and the reference arm, the detector generating output signals in response thereto, wherein said detector has at least two photodetectors connected in series at a common node to provide balanced detection, said detector further including a waveform generator having an output connected between one of the photodetectors and the common node to modify the splitting ratio between the photodetectors as the wavelength of the source is varied in order to compensate for the spectral dependence of the divider, wherein the waveform is generated based on stored calibration information.

18. An OCT system as recited in claim 17, wherein all photodetectors receive combined light.

19. An OCT system as recited in claim 17, wherein at least one photodetector receives no combined light.

20. An OCT system as recited in claim 17, wherein the beam divider and combining optics are fiber optics.

21. An OCT system as recited in claim 17, wherein at least one photodetector receives only source light.

22. An optical coherence tomography (OCT) system, the system comprising:
   a light source arranged to generate a beam of radiation;
   a divider for directing the beam towards at least two interferometers each having its own sample arm;
   optics for combining light from at least one reference arm with sample light from each of the multiple interferometers;

a detector for measuring the combined light from the multiple interferometers, the detector generating output signals in response thereto, wherein said detector has at least three photodetectors, wherein one of the photodetectors receives only source light and does not receive sample light and at least two of the photodetectors receive light from different interferometers, and wherein the step of generating a balanced output includes subtracting the signal from the photodetector with only source light from the signals at the photodetectors with light from multiple interferometers.

23. An OCT system as recited in claim 22, wherein the sample arms of the multiple interferometers are directed towards different locations on the same sample.

24. An OCT system as recited in claim 23, wherein the different locations include two portions of the posterior section of a subject's eye.

25. An OCT system as recited in claim 23, wherein the different locations include a location in the anterior segment and a location in the posterior segment of an eye.

26. An OCT system as recited in claim 22, wherein the sample arms of the multiple interferometers are directed towards locations on both eyes of a subject.

27. An OCT system as recited in claim 22, wherein the system includes a means to spectrally balance the input to the detector.

28. An OCT system as recited in claim 27, wherein the spectral balancing is achieved through the use of a spectral filter prior to data acquisition.

29. An OCT system as recited in claim 22, wherein the system includes a means to spectrally balance the processed signal.

30. An OCT system as recited in claim 29, wherein the means to spectrally balance the processed signal includes digital modification to signals before a digital subtraction process.

31. An OCT system as recited in claim 22, wherein the source light is collected from one of the reference arms.

* * * * *

UNITED STATES PATENT AND TRADEMARK OFFICE
CERTIFICATE OF CORRECTION

PATENT NO. : 8,913,248 B2  
APPLICATION NO. : 13/489368  
DATED : December 16, 2014  
INVENTOR(S) : Utkarsh Sharma et al.

Page 1 of 1

It is certified that error appears in the above-identified patent and that said Letters Patent is hereby corrected as shown below:

In The Specification

In column 1, line 33, delete "architectures" and insert -- architectures. --, therefor.

In column 1, line 67, delete "minor" and insert -- mirror --, therefor.

In column 8, line 5, delete

" $I_{A(+ive)}(\lambda) = \eta_A \cdot S(\lambda) \cdot \cdot TC_{15/85}(\lambda) \cdot TX_{DetA}(\lambda)$ " and insert -- $I_{A(+ive)}(\lambda) = \eta_A \cdot S(\lambda) \cdot TC_{15/85}(\lambda) \cdot TX_{DetA}(\lambda)$ --, therefor.

In column 9, line 61, delete "TX$_{DetA}(\lambda)$)," and insert -- TX$_{DetB}(\lambda)$), --, therefor.

In column 10, line 52, delete "Cl," and insert -- C1, --, therefor.

In column 10, lines 52-53, delete "performance" and insert -- performance. --, therefor.

In column 10, line 59, delete "(1--γ2)*γ1=γ2." and insert -- (1-γ2)*γ1=γ2. --, therefor.

Signed and Sealed this  
Fifteenth Day of September, 2015

Michelle K. Lee  
*Director of the United States Patent and Trademark Office*